(12) United States Patent
Shiota (10) Patent No.: US 10,463,841 B2
(45) Date of Patent: Nov. 5, 2019

(54) BALLOON CATHETER

(71) Applicant: TERUMO KABUSHIKI KAISHA, Shibuya-ku, Tokyo (JP)

(72) Inventor: Hiroyuki Shiota, Fujinomiya (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 589 days.

(21) Appl. No.: 14/852,905

(22) Filed: Sep. 14, 2015

(65) Prior Publication Data

US 2016/0015946 A1    Jan. 21, 2016

Related U.S. Application Data

(63) Continuation of application No. PCT/JP2013/057247, filed on Mar. 14, 2013.

(51) Int. Cl.
*A61M 25/10*    (2013.01)
*A61M 25/00*    (2006.01)
*A61M 25/01*    (2006.01)

(52) U.S. Cl.
CPC .......... *A61M 25/10* (2013.01); *A61M 25/005* (2013.01); *A61M 25/0052* (2013.01);
(Continued)

(58) Field of Classification Search
CPC .................................................. A61M 25/005
See application file for complete search history.

(56) References Cited

U.S. PATENT DOCUMENTS 5,545,134 A     8/1996  Hilaire et al.
5,897,537 A  *  4/1999  Berg ................. A61M 25/0009
                                                        138/134
(Continued)

FOREIGN PATENT DOCUMENTS

EP    1787673 A1    5/2007
EP    2495006 A1    9/2012
(Continued)

OTHER PUBLICATIONS

International Search Report (PCT/ISA/210) dated May 21, 2013, by the Japanese Patent Office as the International Searching Authority for International Application No. PCT/JP2013/057247.
(Continued)

*Primary Examiner* — Bhisma Mehta
*Assistant Examiner* — Matthew A Engel
(74) *Attorney, Agent, or Firm* — Buchanan Ingersoll & Rooney PC (57) ABSTRACT

Provided is a balloon catheter in which a balloon can smoothly deflate even when being pulled. A balloon catheter includes a balloon that can inflate and deflate, a hollow distal shaft that communicates with the balloon and in which an inner shaft is inwardly provided, a hollow intermediate shaft that is connected to a proximal end side of the distal shaft so as to communicate therewith, a hollow proximal shaft that overlaps a proximal end side of the intermediate shaft so as to be connected thereto and that communicates with the intermediate shaft, and a reinforcement body that extends from the proximal shaft to the distal shaft and is fixed to the proximal shaft, in which the intermediate shaft is more flexible than the distal shaft, and in an overlapped portion in which the intermediate shaft and the proximal shaft overlap each other, a non-fixing portion in which the intermediate shaft and the proximal shaft overlap each other without being fixed extends to a distal end side relative to a fixing portion in which the intermediate shaft is fixed to the proximal shaft.

9 Claims, 4 Drawing Sheets

(52) U.S. Cl.
CPC . *A61M 25/0054* (2013.01); *A61M 2025/0059* (2013.01); *A61M 2025/0183* (2013.01); *A61M 2025/1084* (2013.01)

(56) References Cited

U.S. PATENT DOCUMENTS

| | | | |
|---|---|---|---|
| 6,589,207 B1 | 7/2003 | El-Nounou | |
| 2004/0062891 A1 | 4/2004 | Horn et al. | |
| 2012/0302952 A1 | 11/2012 | Kitada et al. | |
| 2012/0303054 A1 | 11/2012 | Wilson et al. | |
| 2013/0150850 A1* | 6/2013 | Ootsubo | A61B 18/1492 606/41 |
| 2013/0178828 A1* | 7/2013 | Takagi | A61M 25/0084 604/506 |
| 2013/0197547 A1* | 8/2013 | Fukuoka | A61B 17/122 606/157 |
| 2013/0217964 A1* | 8/2013 | Kumoyama | A61B 1/0051 600/104 |
| 2013/0304117 A1* | 11/2013 | Sugiyama | A61B 17/0057 606/207 |
| 2013/0304187 A1* | 11/2013 | Yamashita | A61F 2/966 623/1.12 |
| 2013/0331820 A1* | 12/2013 | Itou | A61B 8/12 604/524 |
| 2014/0207171 A1* | 7/2014 | Fujita | A61L 29/048 606/192 |
| 2014/0309533 A1* | 10/2014 | Yamashita | A61M 25/0009 600/463 |
| 2014/0319723 A1* | 10/2014 | Kitada | A61M 25/0021 264/150 |
| 2015/0011827 A1* | 1/2015 | Kinoshita | A61B 17/24 600/114 |

FOREIGN PATENT DOCUMENTS

| | | |
|---|---|---|
| JP | 53-134595 U | 10/1978 |
| JP | 10-503386 A | 3/1998 |
| JP | 2003-517901 A | 6/2003 |
| JP | 2006-500992 A | 1/2006 |
| JP | 2008-264118 A | 11/2008 |
| JP | 2012-115426 A | 6/2012 |
| WO | WO 2004/028611 A1 | 4/2004 |
| WO | WO 2011/108566 A1 | 9/2011 |

OTHER PUBLICATIONS

Communication dated Oct. 31, 2016 issued in the corresponding European Application No. 13877572.1-1501 (7 pages).

* cited by examiner

BALLOON CATHETER

CROSS-REFERENCES TO RELATED APPLICATIONS

This application is a continuation of International Application No. PCT/JP2013/057247 filed on Mar. 14, 2013, the entire content of which is incorporated herein by reference.

TECHNICAL FIELD

The present invention relates to a balloon catheter.

BACKGROUND DISCUSSION

JP-T-2006-500992 discloses an example of a so-called rapid exchange-type balloon catheter including a distal shaft which communicates with a balloon, an intermediate shaft which is connected to a proximal end side of the distal shaft, and a proximal shaft which is connected to a proximal end side of the intermediate shaft. The inside of the distal shaft is provided with an inner shaft through which a guide wire is passed.

The distal shaft and the intermediate shaft are more flexible than the proximal shaft. Therefore, when the balloon gets caught by a stenosed portion or the like in a human body, and an operator pulls the balloon catheter to the proximal end side in the axial direction in order to draw out the balloon therefrom, the distal shaft and the intermediate shaftcan become lengthened compared to the proximal shaft.

SUMMARY

However, when a distal shaft is lengthened, the inner diameter thereof is caused to decrease, thereby narrowing a gap between the distal shaft and an inner shaft configuring a discharge path for an operation fluid inside a balloon and preventing a discharging of the operation fluid from the inside of the balloon. As a result, the balloon is unlikely to deflate.

The present disclosure has an objective thereof to provide a balloon catheter in which a balloon can smoothly deflate even when being pulled.

In order to achieve the above-described object, a balloon catheter according to the present disclosure includes a balloon that can inflate and deflate, a hollow distal shaft that communicates with the balloon and in which an inner shaft is inwardly provided, a hollow intermediate shaft that is connected to a proximal end side of the distal shaft so as to communicate therewith, a hollow proximal shaft that overlaps a proximal end side of the intermediate shaft so as to be connected thereto and that communicates with the intermediate shaft, and a reinforcement body that extends from the proximal shaft to the distal shaft and is fixed to the proximal shaft, in which the intermediate shaft is more flexible than the distal shaft, and in an overlapped portion in which the intermediate shaft and the proximal shaft overlap each other, a non-fixing portion in which the intermediate shaft and the proximal shaft overlap each other without being fixed extends to a distal end side relative to a fixing portion in which the intermediate shaft is fixed to the proximal shaft.

In a balloon catheter according to the present disclosure, an intermediate shaft is more flexible than a distal shaft. Moreover, in the intermediate shaft, since a non-fixing portion extends to a distal end side relative to a fixing portion which is fixed to a proximal shaft in an overlapped portion in which the intermediate shaft and the proximal shaft overlap each other, a portion which is not fixed to the proximal shaft and is able to be lengthened is longer. When the balloon catheter is pulled, the intermediate shaft is preferentially lengthened due to the configuration thereof. As a result, the distal shaft is prevented from being lengthened. Therefore, a gap between the distal shaft and an inner shaft is unlikely to be narrowed. Accordingly, a balloon discharges an operation fluid from the gap therebetween and can be deflated smoothly.

In the overlapped portion, if the fixing portion is positioned at the proximal end of the intermediate shaft, and the non-fixing portion extends to the distal end side relative to the proximal end of the intermediate shaft, when the balloon catheter is pulled, substantially the entirety of the intermediate shaft is lengthened. Therefore, the intermediate shaft is greatly lengthened, and the distal shaft is prevented from being lengthened further. As a result, the gap between the distal shaft and the inner shaft is less likely to be narrowed, and thus, the balloon can be deflated more smoothly.

When a ratio of a length in an axial direction of a portion of the intermediate shaft in which the intermediate shaft and the proximal shaft do not overlap each other and which is on the distal end side relative to the overlapped portion is equal to or less than 50% with respect to a length of the distal shaft in the axial direction, a portion of the intermediate shaft in which the intermediate shaft and the proximal shaft do not overlap each other and which has rigidity lower than that of the overlapped portion decreases. Therefore, pushability for reliably transferring pushing force applied by an operator to the distal end of the balloon catheter is improved.

When a ratio of a length of the intermediate shaft in an axial direction between the proximal end of the distal shaft and the fixing portion is equal to or more than 68% with respect to the length of the distal shaft in the axial direction, the intermediate shaft becomes long. Therefore, the intermediate shaft is greatly lengthened when the balloon catheter is pulled. As a result, the distal shaft is prevented from being lengthened further, and the gap between the distal shaft and the inner shaft is less likely to be narrowed, and thus, the balloon can deflate more smoothly.

When the reinforcement body is a wire including a small diameter portion which is arranged in the proximal shaft, a large diameter portion which is arranged in the intermediate shaft on the distal end side relative to the overlapped portion, and a tapered portion which is arranged in the distal shaft and decreases in diameter toward the distal end side, rigidity of the balloon catheter varies gradually in the axial direction. Therefore, kink resistance for preventing the balloon catheter from bending is improved.

DETAILED DESCRIPTION

Hereinafter, an embodiment of the present invention will be described with reference to the accompanying drawings. Dimension ratios in the drawings are exaggerated for convenience of descriptions, thereby being different from the actual ratios thereof.

Figure 1:
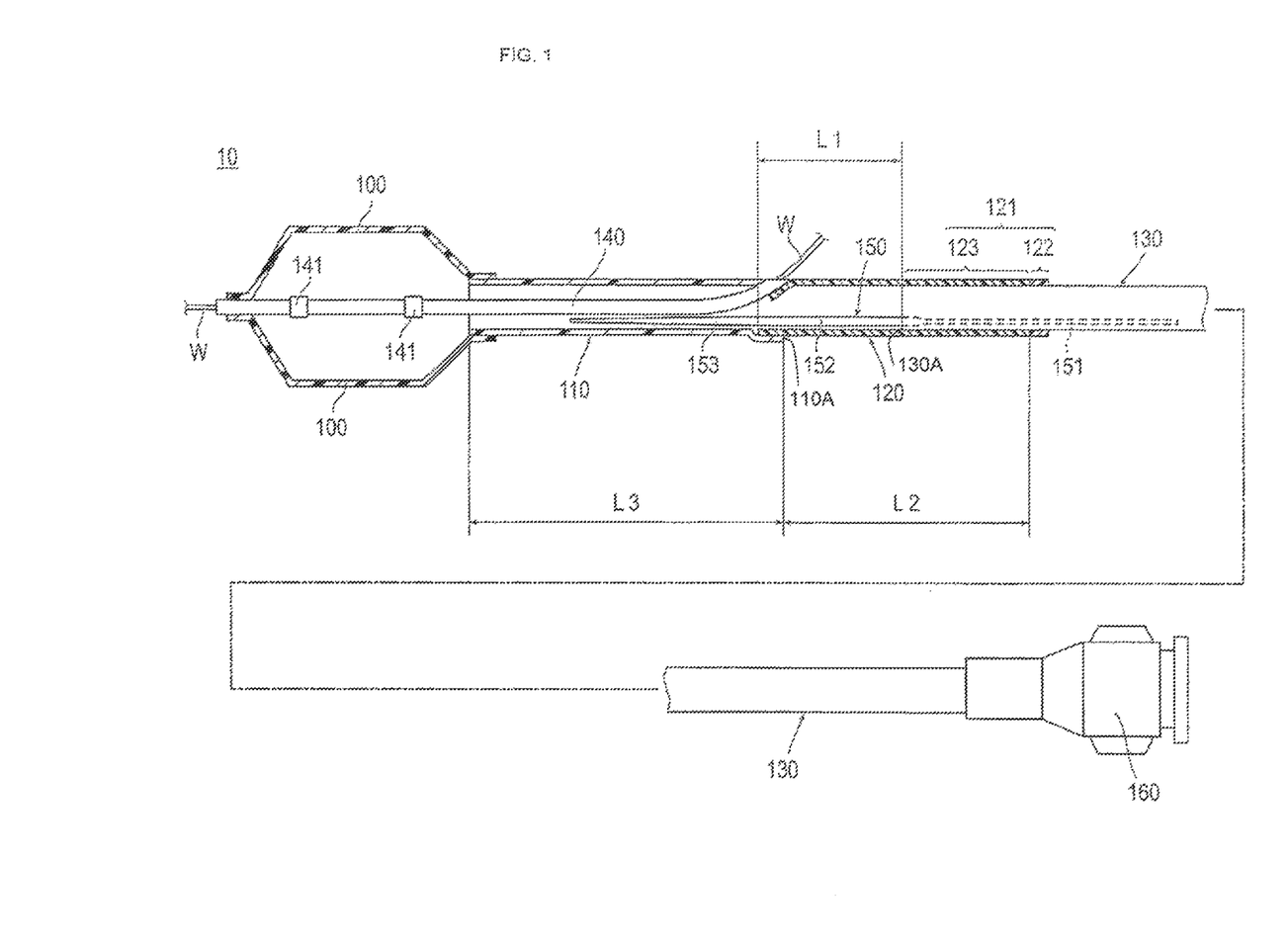
FIG. 1 is a diagram illustrating a schematic configuration of a balloon catheter of an embodiment.

As illustrated in FIG. 1, a balloon catheter 10 of the embodiment includes a balloon 100 which can inflate and deflate, a distal shaft 110 which communicates with the balloon 100, an intermediate shaft 120 which is connected to a proximal end side of the distal shaft 110, and a proximal shaft 130 which is connected to a proximal end side of the intermediate shaft 120.

The balloon catheter 10 includes an inner shaft 140 which allows a guide wire W to be passed through and is provided inside the distal shaft 110, a reinforcement body 150 which extends from the proximal shaft 130 to the distal shaft 110, and a hub 160 which is connected to a proximal end side of the proximal shaft 130.

The balloon 100 surrounds the outer circumference of the inner shaft 140 which protrudes beyond a distal end of the distal shaft 110. A marker 141 having properties of X-ray contrast is attached to the outer circumference of the inner shaft 140 inside the balloon 100. The balloon 100 is folded before dilation.

The distal shaft 110 has a tubular shape. The intermediate shaft 120 has a tubular shape. The distal shaft 110 and the intermediate shaft 120 communicate with each other. A proximal end including a proximal terminus 110a of the distal shaft 110 and a distal end of the intermediate shaft 120 are fixed by using an adhesive or welding, for example.

A proximal end of the inner shaft 140 is arranged on the border between the distal shaft 110 and the intermediate shaft 120. The inner shaft 140 includes opening portions at a distal end and the proximal end. The guide wire W is inserted inside the inner shaft 140 so as to pass through the opening portions provided at the distal end and the proximal end of the inner shaft 140.

The intermediate shaft 120 is more flexible than the distal shaft 110. The intermediate shaft 120 can be made more flexible than the distal shaft 110 by appropriately designing the shape including the diameter, the thickness, or the like. In addition, the intermediate shaft 120 can be made more flexible than the distal shaft 110 by appropriately adjusting the material of the intermediate shaft 120.

The distal shaft 110 and the intermediate shaft 120 can be formed of a thermoplastic resin such as polyamide, polyester, a polyamide elastomer, a polyester elastomer, polyolefin (for example, polyethylene, polypropylene, an ethylene-propylene copolymer, an ethylene-vinyl acetate copolymer, and a cross-linked body or a partially cross-linked body thereof), polyvinyl chloride, polyurethane, and the like.

The proximal shaft 130 has rigidity higher than those of the distal shaft 110 and the intermediate shaft 120. For example, the material forming the proximal shaft 130 can be a metal such as a super elastic alloy like a Ni-Ti alloy or the like; brass; SUS; aluminum; and the like. However, the material is not limited thereto. When other materials having relatively high rigidity are used, for example, the material may be a resin such as polyimide, PEEK, polyvinyl chloride, polycarbonate, and the like.

The proximal shaft 130 has a tubular shape. The proximal shaft 130 and the intermediate shaft 120 communicate with each other.

A distal terminus 130a of the proximal shaft 130 is inserted into the proximal end side of the intermediate shaft 120. In an overlapped portion 121 in which the intermediate shaft 120 and the proximal shaft 130 overlap each other, a non-fixing portion 123 in which the intermediate shaft 120 and the distal terminus 130a of the proximal shaft 130 overlap each other without being fixed extends to a distal end side relative to a fixing portion 122 in which the intermediate shaft 120 is fixed to the proximal shaft 130.

The fixing portion 122 is positioned at a proximal end of the intermediate shaft 120. The non-fixing portion 123 extends to the distal end side relative to the proximal end of the intermediate shaft 120. In the fixing portion 122, the intermediate shaft 120 is fixed to the entirety of the proximal shaft 130 in a circumferential direction by using an adhesive or welding, for example.

The hub 160 can be connected to a device such as a syringe or the like in which an operation fluid is injected or suctioned. The operation fluid suctioned from the device connected to the hub 160 passes through the proximal shaft 130, the intermediate shaft 120, and a gap between the distal shaft 110 and the inner shaft 140 so as to flow into the balloon 100, thereby dilating the balloon 100. For example, the operation fluid is a liquid obtained by diluting an X-ray contrast agent with physiological saline.

In accordance with suctioning performed by the device connected to the hub 160, the operation fluid is discharged from the balloon 100, and the balloon 100 deflates. The operation fluid discharged from the balloon 100 moves to the proximal end side through the gap between the distal shaft 110 and the inner shaft 140, the inside of the intermediate shaft 120, and the inside of the proximal shaft 130.

During a procedure, for example, in which an operator pulls the balloon catheter 10 to the proximal end side in an axial direction in order to draw out the balloon 100, which gets caught by a stenosed portion or the like in a human body, and the distal shaft 110 and the intermediate shaft 120 were to become lengthened compared to the proximal shaft 130 as a result, the inner diameter of the distal shaft 110 and the inner diameter of the intermediate shaft 120 would become small. Furthermore, if the gap between the distal shaft 110 and the inner shaft 140 were to become smaller than the inner diameter of the intermediate shaft 120, the movement of the operation fluid would be bottlenecked. Therefore, preventing the gap between the distal shaft 110 and the inner shaft 140 from being narrowed as much as possible would help to smoothly move the operation fluid.

The reinforcement body 150 is a wire including a small diameter portion 151 which is arranged in the proximal shaft 130, a large diameter portion 152 which is arranged in the intermediate shaft 120 on the distal end side relative to the overlapped portion 121, and a tapered portion 153 which is arranged in the distal shaft 110 and decreases in diameter toward the distal end side.

The material forming the reinforcement body 150 can be a metal such as a super elastic alloy like a Ni—Ti alloy or the like, brass, SUS, aluminum, and the like. However, the material is not limited thereto. When other materials having relatively high rigidity are used, for example, the material may be a resin such as polyimide, polyvinyl chloride, polycarbonate, and the like.

The reinforcement body 150 is fixed onto an inner circumferential surface of the proximal shaft 130 at a proximal end of the large diameter portion 152 by using an adhesive or welding, for example. In portions other than the fixing portion, the reinforcement body 150 is not fixed to the distal shaft 110, the intermediate shaft 120, and the proximal shaft 130.

Operational effects of the present embodiment will be described.

The intermediate shaft 120 is more flexible than the distal shaft 110. Moreover, in the intermediate shaft 120, the non-fixing portion 123 extends to the distal end side relative to the fixing portion 122 in the overlapped portion 121. Therefore, a portion which is not fixed to the proximal shaft 130 and is able to be lengthened is long. When the balloon catheter 10 is pulled, the intermediate shaft 120 is preferentially lengthened due to the configuration thereof. As a result, the distal shaft 110 is prevented from being lengthened. Therefore, the gap between the distal shaft 110 and the inner shaft 140 is unlikely to be narrowed. Accordingly, the balloon 100 discharges the operation fluid from the gap therebetween and can be deflated smoothly.

In the overlapped portion 121, the fixing portion 122 is positioned at the proximal end of the intermediate shaft 120, and the non-fixing portion 123 extends to the distal end side relative to the proximal end of the intermediate shaft 120. When the balloon catheter 10 is pulled, substantially the entirety of the intermediate shaft 120 is lengthened due to the configuration thereof. Therefore, the intermediate shaft 120 is greatly lengthened, and the distal shaft 110 is prevented from being lengthened further. As a result, the gap between the distal shaft 110 and the inner shaft 140 is less likely to be narrowed, and thus, the balloon 100 can be deflated more smoothly.

As the present embodiment, when a length L1 in the axial direction of a portion in which the intermediate shaft 120 and the proximal shaft 130 do not overlap each other and which is on the distal end side relative to the overlapped portion 121 is short, for example, when a ratio of the length L1 to a length L3 of the distal shaft 110 in the axial direction is equal to or less than 50%, the portion in which the intermediate shaft 120 and the proximal shaft 130 do not overlap each other and which has rigidity lower than that of the overlapped portion 121 decreases. Therefore, pushability for reliably transferring pushing force applied by an operator to the distal end of the balloon catheter 10 is improved.

In the present embodiment, the intermediate shaft 120 is long, for example, a ratio of a length L2 of the intermediate shaft 120 to the length L3 of the distal shaft 110 in the axial direction is equal to or greater than 68%. Therefore, the intermediate shaft 120 is greatly lengthened when the balloon catheter 10 is pulled. As a result, the distal shaft 110 is prevented from being lengthened further, and the gap between the distal shaft 110 and the inner shaft 140 is less likely to be narrowed, and thus, the balloon 100 can be deflated more smoothly.

Since rigidity of the balloon catheter 10 increases by providing the reinforcement body 150, pushability is improved.

The reinforcement body 150 is attached to the balloon catheter 10 so as to arrange the small diameter portion 151 in the proximal shaft 130, to arrange the large diameter portion 152 in the intermediate shaft 120 on the distal end side relative to the overlapped portion 121, and to arrange the tapered portion 153 in the distal shaft 110. According to the configuration thereof, rigidity of the balloon catheter 10 varies gradually in the axial direction. Therefore, kink resistance for preventing the balloon catheter 10 from bending is improved.

Since the reinforcement body 150 is partially fixed to the balloon catheter 10 at one place only, movement of the balloon catheter 10 is unlikely to be restricted by the reinforcement body 150 and is able to be flexibly bent compared to a case of being fixed at multiple places.

EXAMPLE

The inventors measured the lengthened states of the intermediate shaft 120, changes in rigidity of the balloon catheter 10 in the axial direction, and pressing force at the distal end when the balloon catheter 10 was pushed in, by using experimental samples.

Lengthened states will be described with reference to FIGS. 2 and 3.

Figure 2:
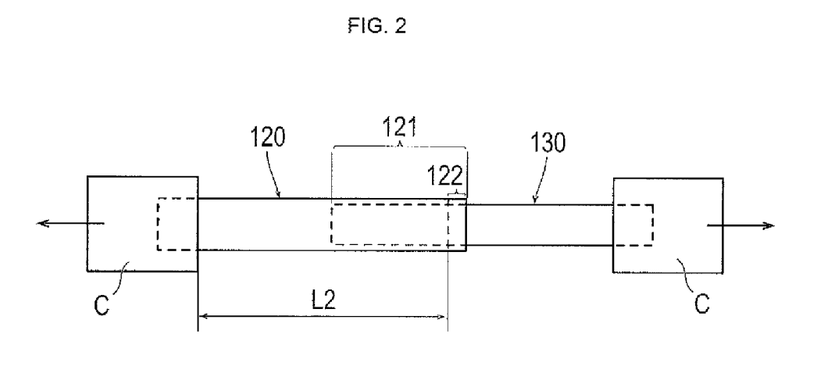
FIG. 2 is a diagram schematically illustrating a tension test of an intermediate shaft and a proximal shaft of the balloon catheter of the embodiment.
Figure 3:
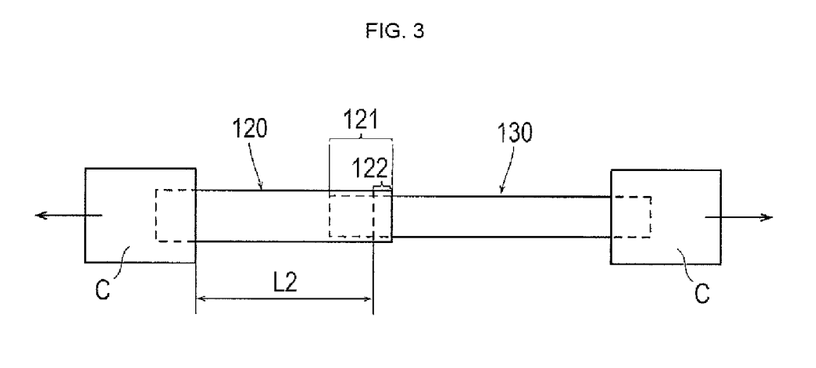
FIG. 3 is a diagram schematically illustrating another tension test of the intermediate shaft and the proximal shaft of the balloon catheter of the embodiment.

As illustrated in FIGS. 2 and 3, the inventors pulled a plurality of the experimental intermediate shafts 120 having lengths different from one another in the axial direction in a state of being fixed to the experimental proximal shaft 130 at the fixing portion 122 similarly to the embodiment and measured lengthened states thereof when being ruptured, by using a tension tester. The inventors carried out tension tests three times for each of the plurality of the experimental intermediate shafts 120 having lengths different from one another. The proximal shaft 130 fixed to each of the plurality of intermediate shafts 120 was the same.

In the plurality of experimental intermediate shafts 120, the lengths L2 in the axial direction from a chuck C for grasping an end portion of the intermediate shaft 120 to the fixing portion 122 were respectively 130 mm, 150 mm, 170 mm, 190 mm, 220 mm, and 240 mm. In the lengths L2, the length of a portion on the chuck C side relative to the overlapped portion 121 was the same in the plurality of intermediate shafts 120.

The configurations other than the length L2 were the same in the plurality of experimental intermediate shafts 120. The material forming the experimental intermediate shaft 120 was nylon 12. The inventors carried out the tension tests by using the intermediate shaft 120 subjected to annealing processing at 80° C. for one hour. The inner diameter of the experimental intermediate shaft 120 was 0.67 mm, and the outer diameter thereof was 0.84 mm.

The material forming the proximal shaft 130 used in the tension test was SUS304. In the proximal shaft 130 used in the tension test, texture processing was performed on an outer circumference surface at a position corresponding to the fixing portion 122. The inner diameter of the proximal shaft 130 used in the tension test was 0.46 mm, and the outer diameter thereof was 0.64 mm.

A separation distance between the chucks C was 300 mm. A tension speed occurring by the chuck C was 100 mm/min.

Figure 4:
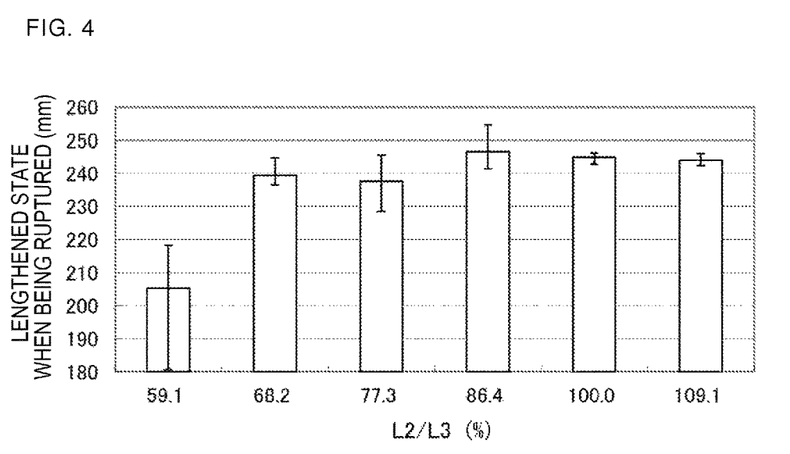
FIG. 4 is a graph illustrating a result acquired through the tension test.

FIG. 4 shows the result of the tension test. The horizontal axis in FIG. 4 indicates values which were obtained by dividing each of the lengths L2 of the plurality of intermediate shafts 120 used in the tension test by the length L3 of the distal shaft 110 in the axial direction (refer to FIG. 1) in the experimental balloon catheter 10. In the present Example, the length L3 was 220 mm. The lengthened state on the vertical axis in FIG. 4 was the average value of the lengthened states obtained through the three tension tests carried out with each of the intermediate shafts 120.

According to FIG. 4, it has been found that the lengthened state of the intermediate shaft 120 enlarges when the intermediate shaft 120 is long and a ratio of the length L2 of the intermediate shaft 120 to the length L3 of the distal shaft 110 is equal to or greater than 68%. When the balloon catheter 10 is pulled, the intermediate shaft 120 is greatly lengthened. Therefore, the distal shaft 110 is prevented from being lengthened, and the gap between the distal shaft 110 and the inner shaft 140 is unlikely to be narrowed. Accordingly, the balloon 100 can be deflated smoothly.

Subsequently, changes in rigidity of the balloon catheter 10 in the axial direction will be described.

The inventors measured changes in rigidity in the axial direction by carrying out a three-point bending test for each of a plurality of places in the experimental balloon catheter 10 separated from each other in the axial direction.

The length L3 of the distal shaft 110 in the axial direction in the balloon catheter 10 used in measurement of the rigidity was 220 mm, the length L2 of the same distal shaft 110 in the axial direction from the proximal end to the fixing portion 122 was 220 mm, and the length of the overlapped portion 121 in the axial direction in the same balloon catheter 10 was 110 mm.

In the measurement places where the three-point bending tests were carried out, the separation distances in the axial direction from the distal end of the balloon catheter 10 were respectively at places of 40 mm, 80 mm, 120 mm, 160 mm, 200 mm, 240 mm, 280 mm, 320 mm, and 360 mm. In the three-point bending test, the balloon catheter 10 was supported at a width of one inch, and the balloon catheter 10 was bent by applying force in a direction orthogonal to the axial direction at the measurement place which was the center of the width.

As Comparison Examples, the inventors measured changes in rigidity in the axial direction similarly in a rapid exchange-type balloon catheter commercially available.

Figure 5:
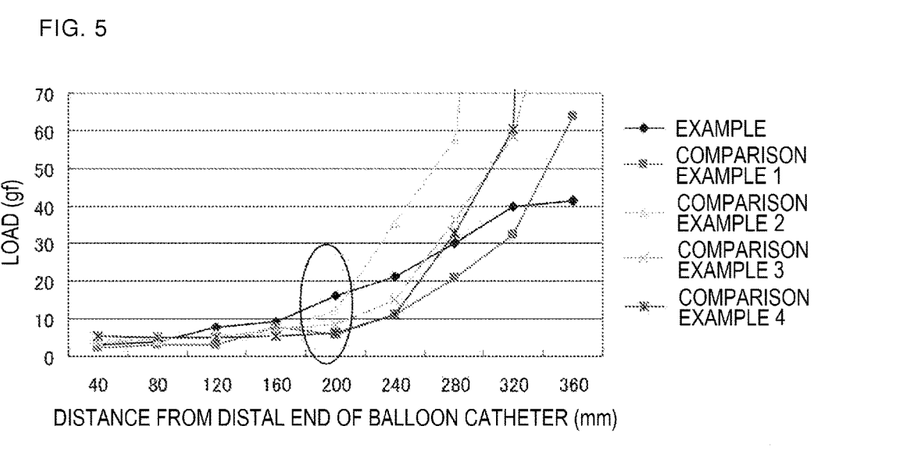
FIG. 5 is a graph illustrating changes in rigidity of the balloon catheter of the embodiment and the balloon catheters of Comparison Examples in an axial direction.

FIG. 5 shows the measurement result of changes in rigidity in the axial direction. The vertical axis in FIG. 5 indicates loads applied through the three-point bending test. The loads were obtained by applying force in the direction orthogonal to the axial direction so as to bend each of the balloon catheters 10 in Example and Comparison Examples 1 to 4 while displacing the force-applied measurement place by 0.3 mm.

As shown in the portion circled by an ellipse in FIG. 5, in the balloon catheters of Comparison Examples 1 to 4, changes in rigidity were remarkable in the vicinity of the opening portion provided on the outer circumference through which the guide wire W was passed. In contrast, in the experimental balloon catheter 10 of Example, it was found that rigidity varied gradually in the axial direction. Although there is a possibility of an occurrence of bending at a place where rigidity greatly varies, since rigidity varies gradually in the axial direction in the balloon catheter 10 of Example, kink resistance is excellent.

Subsequently, descriptions will be given regarding pressing force at the distal end when the balloon catheter 10 is pushed from the proximal end side to the distal end side.

The inventors measured the pressing force at the distal end for each of the three experimental balloon catheters 10 in the intermediate shaft 120 having the lengths L1 different from one another (refer to FIG. 1).

Here, the lengths L1 were respectively 110 mm, 150 mm, and 220 mm. In the three experimental balloon catheters 10, the lengths L3 of the distal shafts 110 in the axial direction were commonly 220 mm, and the lengths of the overlapped portions 121 in the axial direction were commonly 110 mm.

The inventors measured the pressing force at the distal end by inserting and pushing the experimental balloon catheter 10 into a model of a blood vessel, and causing the distal end of the balloon catheter 10 to press a force measurement sensor which was installed inside the model of a blood vessel. The inventors measured the pressing force at the distal end three times for each of the three experimental balloon catheters 10 having the lengths L1 different from one another.

Figure 6:
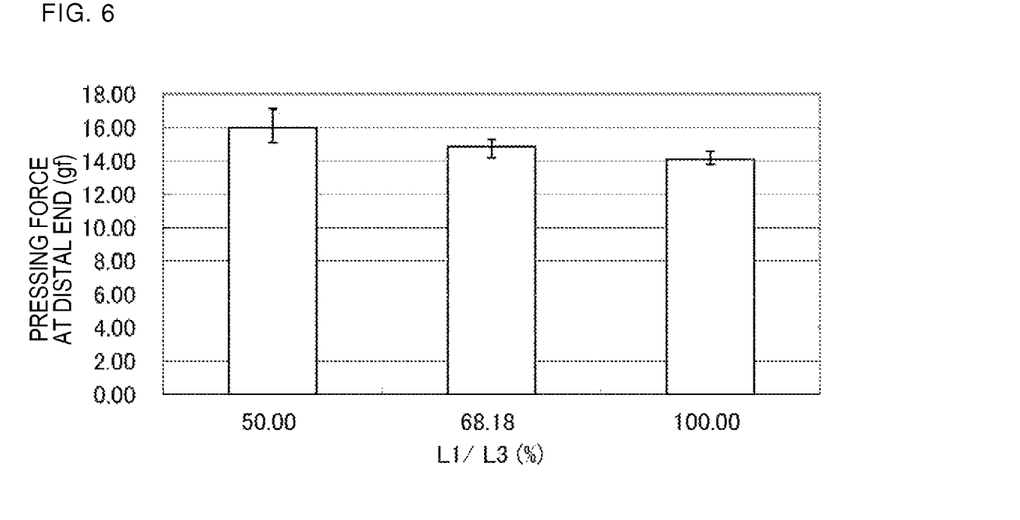
FIG. 6 is a graph illustrating pressing force at a distal end of the balloon catheter measured by varying the length of the intermediate shaft on the distal end side relative to the overlapped portion.

FIG. 6 shows the measurement result of the pressing force. The horizontal axis in FIG. 6 indicates values which were obtained by dividing the length L1 in each balloon catheter 10 used in measurement of the pressing force by the length L3 of the distal shaft 110 in the axial direction in the balloon catheter 10. Here, L3 was 220 mm. The pressing force on the vertical axis in FIG. 6 was the average value of the results obtained through the measurement of the pressing force carried out three times for each balloon catheter 10.

According to FIG. 6, it has been found that the pressing force at the distal end is greater in the balloon catheter 10 having the shorter length L1. As the length L1 becomes shorter, the portion in which the intermediate shaft 120 and the proximal shaft 130 do not overlap each other and which has rigidity lower than that of the overlapped portion 121 decreases. Therefore, it is assumed that pushability is improved.

The inventors measured the pressing force of the balloon catheter 10 at the distal end in a similar manner as described above for each of the plurality of experimental balloon catheters 10 having the lengths of the tapered portions 153 of the reinforcement body 150 in the axial direction different from one another.

Here, the lengths of the tapered portions 153 in the axial direction in the plurality of experimental balloon catheters 10 were respectively 160 mm, 190 mm, 220 mm, 250 mm, and 280 mm. In the plurality of balloon catheters 10, the lengths L3 of the distal shaft 110 in the axial direction were commonly 220 mm, and the lengths L1 of the portion of the intermediate shaft 120 in the axial direction on the distal end side relative to the overlapped portion 121 were commonly 110 mm.

As Comparison Examples, the inventors measured the pressing force at the distal end similarly in the rapid exchange-type balloon catheter 10 commercially available.

Figure 7:
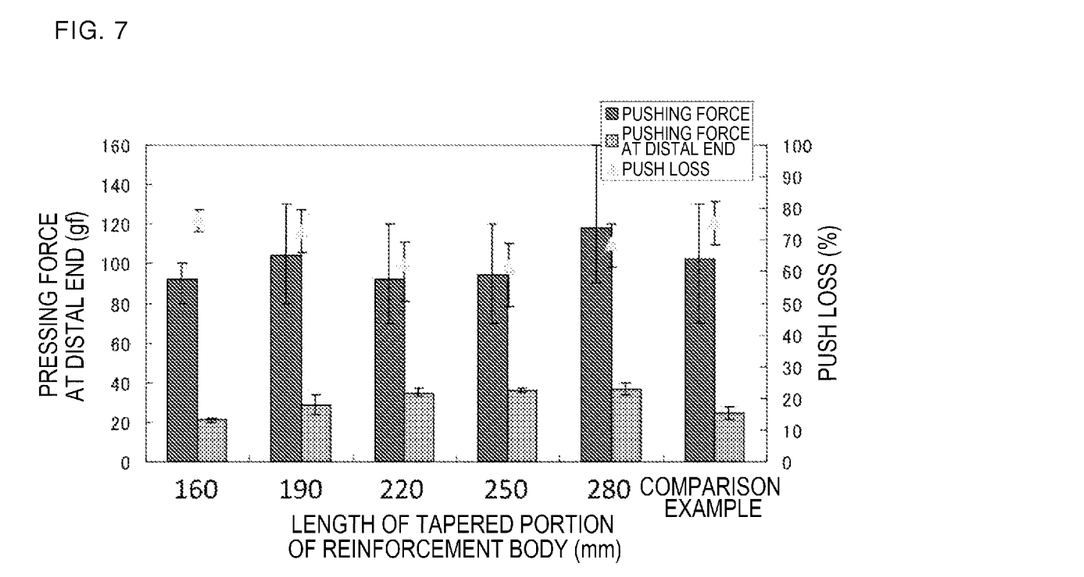
FIG. 7 is a graph illustrating pressing force at the distal end of the balloon catheter, pushing force applied to the balloon catheter, and push loss which is a ratio of a difference between the pressing force and the pushing force, measured by varying the length of a tapered portion of a reinforcement body.

FIG. 7 shows the measurement result of the pressing force at the distal end when the length of the tapered portion 153 is varied. When the length of the tapered portion 153 in the axial direction is longer than 160 mm, and the reinforcement body 150 extends on the distal end side relative to the center of the distal shaft 110 in the axial direction, compared to a case where the length of the tapered portion 153 in the axial direction is 160 mm, and the distal end of the reinforcement body 150 is positioned on the proximal end side relative to the center of the distal shaft 110 in the axial direction, it has been found that the pressing force of the balloon catheter 10 at the distal end is greater than 10% or more.

The detailed description above describes a balloon catheter. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims. For example, the position of the fixing portion in which the intermediate shaft is fixed to the proximal shaft is not limited to the proximal end of the intermediate shaft as the above-described embodiment. The present invention includes a form in which the intermediate shaft is fixed to the proximal shaft on the distal end side relative to the proximal end thereof.

REFERENCE SIGNS LIST 10 balloon catheter,
100 balloon,
110 distal shaft,
120 intermediate shaft,
121 overlapped portion,
122 fixing portion,
123 non-fixing portion,
130 proximal shaft,
140 inner shaft,
141 marker,
150 reinforcement body,
151 small diameter portion,
152 large diameter portion,
153 tapered portion,
160 hub, and
W guide wire.

What is claimed is:

1. A balloon catheter, comprising:
a balloon that can inflate and deflate;
a hollow distal shaft that communicates with the balloon and in which an inner shaft is inwardly provided;
a hollow intermediate shaft that is connected to a proximal end side of the distal shaft so as to communicate therewith;
a hollow proximal shaft that overlaps a proximal end side of the intermediate shaft so as to be connected thereto and that communicates with the intermediate shaft; and
a reinforcement body that extends from the proximal shaft to the distal shaft and is fixed to the proximal shaft,
wherein the intermediate shaft is more flexible than the distal shaft,
wherein in an overlapped portion in which the intermediate shaft and the proximal shaft overlap each other, a non-fixing portion in which the intermediate shaft and the proximal shaft overlap each other without being fixed extends to a distal end side relative to a fixing portion in which the intermediate shaft is fixed to the proximal shaft, and the non-fixing portion includes a distal terminus of the proximal shaft which is positioned inside the intermediate shaft and proximal to a proximal terminus of the distal shaft.

2. The balloon catheter according to claim 1,
wherein in the overlapped portion, the fixing portion is positioned at a proximal end of the intermediate shaft, and the non-fixing portion extends to the distal end side relative to the proximal end of the intermediate shaft.

3. The balloon catheter according to claim 1,
wherein a ratio of a length in an axial direction of a portion of the intermediate shaft in which the intermediate shaft and the proximal shaft do not overlap each other and which is on the distal end side relative to the overlapped portion is equal to or less than 50% of a length of the distal shaft in the axial direction.

4. The balloon catheter according to claim 1,
wherein a ratio of a length of the intermediate shaft in an axial direction between the proximal terminus of the distal shaft and the fixing portion, is equal to or more than 68% of a length of the distal shaft in the axial direction.

5. The balloon catheter according to claim 4,
wherein the reinforcement body is a wire including a small diameter portion which is arranged in the proximal shaft, a large diameter portion which is arranged in the intermediate shaft on the distal end side relative to the overlapped portion, and a tapered portion which is arranged in the distal shaft and decreases in diameter toward the distal end side.

6. The balloon catheter according to claim 1,
wherein the reinforcement body is a wire including a small diameter portion which is arranged in the proximal shaft, a large diameter portion which is arranged in the intermediate shaft on the distal end side relative to the overlapped portion, and a tapered portion which is arranged in the distal shaft and decreases in diameter toward the distal end side.

7. The balloon catheter according to claim 1,
wherein the non-fixing portion has a tubular shape and a central axis of the tubular shape of the non-fixing portion from a distal end of the non-fixing portion to a proximal end of the non-fixing portion is collinear with a central axis of an outer cylindrical surface of the proximal shaft.

8. A balloon catheter, comprising:
a balloon that can inflate and deflate;
a hollow distal shaft that communicates with the balloon and in which an inner shaft is inwardly provided;
a hollow intermediate shaft that is connected to a proximal end side of the distal shaft so as to communicate therewith;
a hollow proximal shaft that overlaps a proximal end side of the intermediate shaft so as to be connected thereto and that communicates with the intermediate shaft; and
a reinforcement body that extends from the proximal shaft to the distal shaft and is fixed to the proximal shaft,
wherein the intermediate shaft is more flexible than the distal shaft, and
wherein in an overlapped portion in which the intermediate shaft and the proximal shaft overlap each other, a non-fixing portion in which 1) the intermediate shaft and the proximal shaft overlap each other without being fixed, and 2) the proximal shaft is not fixed to the distal shaft, extends to a distal end side relative to a fixing portion in which the intermediate shaft is fixed to the proximal shaft, and a distal terminus of the proximal shaft is positioned inside the intermediate shaft and proximal to a proximal terminus of the distal shaft.

9. The balloon catheter according to claim 8,
wherein the non-fixing portion has a tubular shape and a central axis of the tubular shape of the non-fixing portion from a distal end of the non-fixing portion to a proximal end of the non-fixing portion is collinear with a central axis of an outer cylindrical surface of the proximal shaft.

* * * * *